US00PP12996P2

(12) United States Plant Patent
Zary

(10) Patent No.: US PP12,996 P2
(45) Date of Patent: Sep. 24, 2002

(54) MINIATURE ROSE PLANT NAMED 'JACMARNE'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 17 days.

(21) Appl. No.: 09/724,686

(22) Filed: Nov. 28, 2000

(51) Int. Cl.[7] ..... A01H 5/00
(52) U.S. Cl. ..... Plt./129
(58) Field of Search ..... Plt./116, 122, 123, Plt./129, 141, 149, 150, 151

*Primary Examiner*—Howard J. Locker
(74) *Attorney, Agent, or Firm*—Klarquist Sparkman, LLP

(57) ABSTRACT

Miniature rose plant having long, narrow foliage; vigorous, well branched, rounded growth habit; fragrant flowers; ease of propagation by softwood or hardwood cuttings; excellent disease resistance; and deep, near red flower color with high petal count.

1 Drawing Sheet

The present invention relates to a new and distinct variety of rose plant of the miniature class which was originated by me by crossing La Marne (unpatented) with an unnamed seedling whose parents were China Doll×MORchari U.S. Plant Pat. No. 5,975).

The primary objective of this breeding was to produce a new rose variety having the rounded compact habit, vigorous growth and disease resistance of the female parent combined with the deep pink flower color, high petal count and fragrance of the male parent. The objective was substantially achieved, along with other desirable improvements, as evidenced by the following unique combination of characteristics that are outstanding in the new variety and that distinguish it from its parents, as well as from all other varieties of which I am aware:

1. Long, narrow foliage with 7 to 9 leaflets;
2. Vigorous, well branched, rounded, growth habit;
3. Fragrant flowers;
4. Ease of propagation by softwood or hardwood cuttings;
5. Excellent disease resistance; and
6. Deep, near red flower color with high petal count.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—La Marne. (Not patented).

*Pollen parent.*—Unnamed seedling (China Doll× MORchari, U.S. Plant Pat. No. 5,975).

Classification:

*Botanical.*—*Rosa hybrida.*

*Commercial.*—Miniature.

FLOWER

Observations made from specimens grown in a garden environment at Somis, Calif. in January, 1998–November, 2000.

Blooming habit: Continuous.

Bud:

*Size.*—About ½ inch long when the petals start to unfurl.

*Form.*—The bud form is long, pointed ovoid.

*Color.*—When sepals first divide, bud color is Red Group 53B. The bud often has a lighter streak along the mid-rib of Red-Purple Group 63C. When half blown, the upper sides of the petals are Red Group 53B, occasionally with petals showing a white streak (White Group 155D); and the lower sides of the petals are Red-Purple Group 63C, often with a lighter area along the mid-rib of Red-Purple Group 63D.

*Sepals.*—Color: Yellow-Green Group 147C. Surface texture: Covered in fine hairs. There are three lightly to normally appendaged sepals. There are two unappendaged sepals with hairy edges.

*Receptacle.*—Color: Yellow-Green Group 147C but often colored Greyed-Purple Group 184B when exposed to bright light. Shape: Funnel. Size: Small, 3/16"×3/16". Surface: Hairy.

*Peduncle.*—Length: Short, averaging about 2 inches. Surface: Smooth with an occassional gland. Color: Between Green Group 139B and C, but often colored Red-Purple Group 184B when exposed to bright sunlight. Strength: Bending, slender.

Bloom:

*Size.*—Small. Average open size is 2 to 2½ inches.

*Borne.*—Several together in a rounded cluster of 5–7 blooms.

*Stems.*—Strength: Strong. Average length is about 8–12 inches.

*Form.*—When first open: Bloom is high centered. Permanence: Flattens, outer petal edges curl slightly.

*Petalage*.—Number of petals under normal conditions: 35–40.

*Color*.—The upper sides of the petals are Red Group 53B, with petals occasionally showing a white streak (White Group 155D). The reverse sides of the petals are Red-Purple Group 63C, often with a lighter area along the mid-rib of Red Purple Group 63D. The base of each petal has on the upper surface a comparitively large 5/16"×1/4" Yellow Group 11C colorspot with a 1/16"×1/16" Yellow Group 11B area at the top of the base. The petal reverse has a 1/8"×1/8" colorspot of Yellow Group 11B. The major color on the upper side is Red Group 53B.

*Variegations*.—There are variegations on the upper surface comprising streaks of White Group 155D along the mid-rib of some petals.

*Discoloration*.—The general tonality at the end of the first day: No change. At the end of the third day: Fades to Red-Purple Group 63B followed by petal drop by day five.

*Fragrance*.—Moderate, lilac.

Petals:

*Texture*.—Thin.

*Shape*.—Oval to deltoid.

*Form*.—Tips slightly recurved.

*Arrangement*.—Imbricated. Petaloids in the center are many (3–10). Color is the same as the petals. Size varies from 3/4"×1/4" to 1/2"×1/8".

*Persistence*.—Petals drop off cleanly before drying.

*Lastingness*.—On the plant: Short (about 5 days). As a cut flower: Short (about 6 days).

Reproductive parts:

*Anthers*.—Size: Medium. Quantity: Many. Color: Yellow-Orange Group 22D. Arrangement: Regular around styles, mixed with petaloids.

*Filaments*.—Color: Yellow Group 11C.

*Pollen*.—Color: No pollen has been extracted and plant does not set hips in the garden or by artificial (hand) pollenation. It appears sterile.

*Styles*.—Color: Red-Purple Group 61D.

*Stigmas*.—Color: Yellow-White Group 158A.

Plant:

*Form*.—Bush.

*Growth*.—Vigorous, branching and compact. At maturity after on full season of growth, height is 2½ feet, width is 2 feet.

Foliage: Number of leaflets on normal mid-stem leaves: 7 or 9.

*Size*.—Narrow and long (5–6 inches long×2½–3 inches wide).

*Quantity*.—Abundant.

*Color*.—Old foliage: Upper surface: Green Group 136A. Lower surface: Green Group 138B. New foliage: Upper surface: Greyed-Red Group 178A. Lower surface: Greyed-Red Group 178A.

Leaflets:

*Shape*.—Lanceolate.

*Texture*.—Leathery, glossy.

*Edge*.—Serrated.

*Serration*.—Single, small.

*Petiole rachis*.—Color: Green Group 136B (mature leaf).

*Petiole underside*.—Rough, with prickles and many glands.

*Stipules*.—Medium, serrated (about ½ inch).

*Disease resistance*.—Resistant to mildew and rust; susceptible to blackspot under normal growing conditions.

Wood:

*New wood*.—Color: Greyed-Red Group 178B. Bark: Smooth.

*Old wood*.—Color: Green Group 139A. Bark: Smooth.

Prickles:

*Quantity*.—On main canes from base: Ordinary. On laterals from main canes: Ordinary.

*Form*.—Medium, hooked downward.

*Color when young*.—Greyed-Purple Group 184A.

*Color when mature*.—Greyed-Orange Group 177A.

Small prickles:

*Quantity*.—On main stalks: None. On laterals: None

I claim:

1. A new and distinct variety of rose plant of the miniature class, substantially as herein shown and described, characterized particularly by its long, narrow foliage; vigorous, well branched, rounded growth habit; fragrant flowers; ease of propagation by softwood or hardwood cuttings; excellent disease resistance; and deep, near red flower color with high petal count.

* * * * *

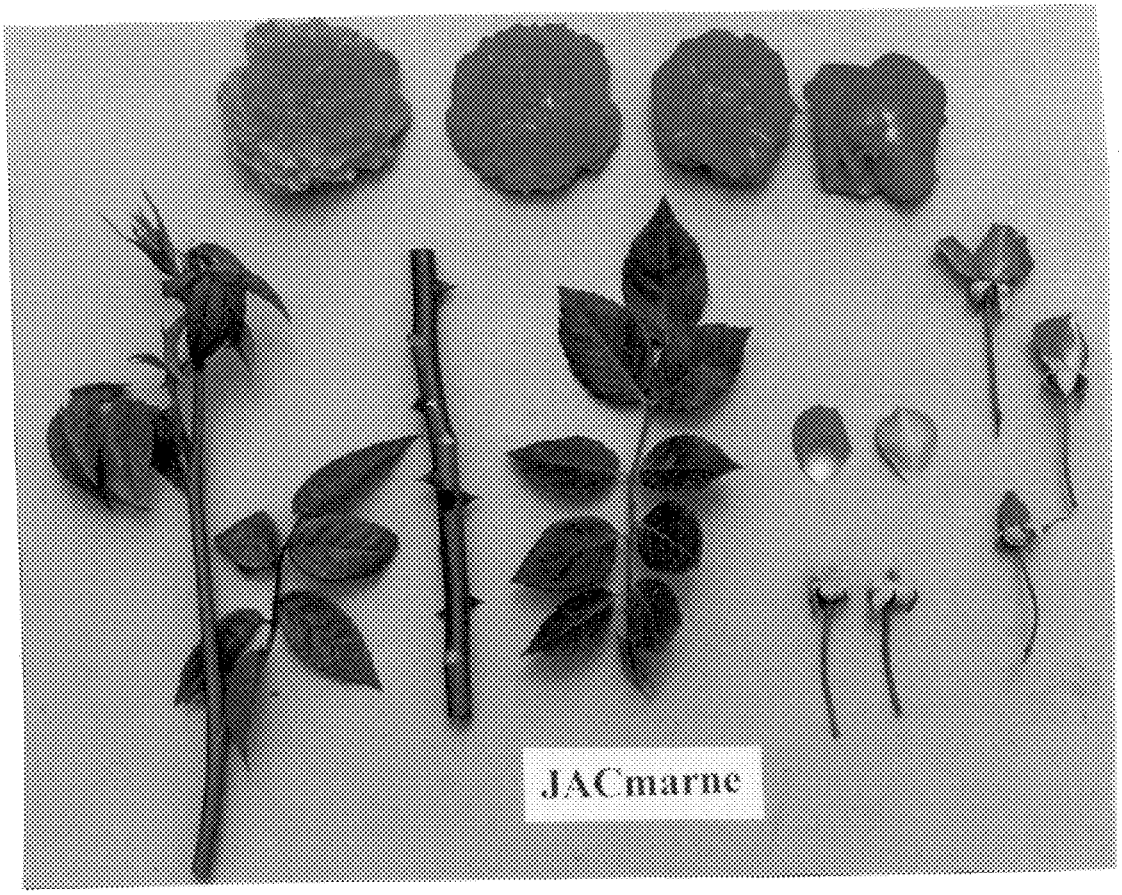
JACmarne